United States Patent [19]
Low et al.

[11] Patent Number: 5,994,320
[45] Date of Patent: Nov. 30, 1999

[54] ANTISENSE OLIGONUCLEOTIDES AND METHODS FOR TREATING CENTRAL NERVOUS SYSTEM TUMORS

[75] Inventors: Walter C. Low, Shorewood; Eric P. Flores; Walter A. Hall, both of Minneapolis; Lan Chiang, Plymouth; John A. Conrad, Lino Lakes, all of Minn.

[73] Assignee: Regents of the University of Minnesota, Minneapolis, Minn.

[21] Appl. No.: 08/985,583

[22] Filed: Dec. 5, 1997

Related U.S. Application Data

[63] Continuation of application No. 08/437,150, May 2, 1995, abandoned, which is a continuation-in-part of application No. 08/383,733, Feb. 6, 1995, abandoned.

[51] Int. Cl.$^6$ .............................. A61K 48/00; C12Q 1/68; C12N 5/12; C07H 21/04
[52] U.S. Cl. ................................. 514/44; 435/6; 435/366; 536/23.1; 536/24.5
[58] Field of Search ............................. 514/44; 536/23.1, 536/24.31, 24.5; 435/6, 91.1, 366, 375

[56] References Cited

U.S. PATENT DOCUMENTS

| | | |
|---|---|---|
| 4,699,877 | 10/1987 | Cline et al. . |
| 5,098,890 | 3/1992 | Gewirtz et al. . |
| 5,585,479 | 12/1996 | Hoke et al. ............................. 536/24.5 |

FOREIGN PATENT DOCUMENTS

| | | |
|---|---|---|
| 90/05445 | 5/1990 | WIPO . |
| 92/08729 | 5/1992 | WIPO . |
| 92/20348 | 11/1992 | WIPO . |
| 93/09789 | 5/1993 | WIPO . |

OTHER PUBLICATIONS

Rojanasakul, Antisense oligonucleotide therapeutics: drug delivery and targeting, Advanced Drug Delivery Reviews, vol. 18, pp. 115–131, 1996.
Gewirtz et al., Facilitating oligonucleotide delivery: Helping antisense deliver on its promise, Proc. Natl. Acad. Sci., vol. 93, pp. 3161–3163, Apr. 1996.
Branch, A good antisense is hard to find, TIBS, vol. 23, pp. 45–50, Feb. 1998.
Golden, Of mice and men: Don't blame the rodents, Time, vol. 151 (19), p. 44, May 18, 1998.
Baserga et al., Ann NY Acad. 660:64 (1992), Inhibition of Cell Cycle Progression by Antisense Oligodeoxynucleotides.
Behl et al., Neurosurgery 33:679 (1993), Autocrine Growth Regulation in Neuroectodermal Tumors as Detected with Oligodeoxynucleotide Antisense Molecules.
Caracciolo et al., J. of Clin. Invest. 85:55 (1990), Stage-related Proliferative Activity Determines c–myb Functional Requirements During Normal Human Hematopoiesis.
Cuddihy et al., Mol. Cell Biol. 13:3505 (1993), Only the DNA Binding and Transactivation Domains of c–myb are Required to Block Terminal Differentiation of Murine Erythroleukemia Cells.
Ferrari et al., Cell Growth and Differention 1:543 (1990), Differential Effects of c–myb and c–fes Antisense Oligodeoxynucleotides on Granulocytic Differentiation of Human Myeloid Leukemia HL60 Cells.
Grasser et al., Protein Truncation is Required for the Activation of the c–my Proto–oncogene, J. Cell Physiol. 131:43 (1987).
Iyer et al., 3H–1,2–Benzo dithiole–3–one 1,1–dioxide as an Improved Sulfurizing Reagent in the Solid Phase Synthesis of Oligodeoxyribonucleoside Phosphorothioates, J. Am. Chem. Soc. 112:1253 (1990).
Majello et al., PNAS 83:9636 (1986), Human c–myb protooncogene: Nucleotide Sequence of cDNA and Organization of the Genomic Locus.
Murphy et al., Mol. Endocrin. 6:877 (1992), Phosphorothioate Antisense Oligonucleotides Against Basic Fibroblast Growth Factor Inhibit Anchorage–dependent and Anchorage–independent Growth of a Malignant Glioblastoma Cell Line.
Nitta et al., Neurosurgery 34:309 (1994), Specific Inhibition of C–SIS Protein Synthesis and Cell Proliferation with Antisense Oligonucleotides in Human Glioma Cells.
Ku et al., J. of Biol. Chem. 268:2255 (1993), C–myb Transactivates cdc2 Expression via myb Binding Sites in the 5' Flanking Region of the Human cdc2 Gene.
Raschella et al., Cancer Res. 52:4221 (1992), Inhibition of Proliferation by C–myb Antisense RNA and Oligodeoxynucleotides in Transformed Neuroectodermal Cell Lines.
Stec et al., J. of Am. Chem. Soc. 106:6077 (1984), Automated Solid Phase Synthesis, Separation, and StereoChemistry of Phosphorothioate Analogues of Oligodeoxyribonucleotides.
Thiele et al., Mol. Cell Biol. 8:1677 (1988), Regulation of C–myb Expression in Human Neuroblastoma Cells During Retinoic Acid Induced Differentiation.
Thompson et al., Nature 319:374 (1986), Expression of the C–myb Proto–oncogene During Cellular Proliferation.

(List continued on next page.)

*Primary Examiner*—Nancy Degen
*Assistant Examiner*—Andrew Wang
*Attorney, Agent, or Firm*—Merchant & Gould P.C.

[57] ABSTRACT

The invention provides compositions and methods for treating primary brain cancer. The compositions include at least one antisense oligonucleotide that inhibits the proliferation of primary brain cancer cells. The antisense oligonucleotides are preferably complementary to and hybridize to a mRNA encoding c-myb. A method of the invention involves treating patients with primary brain cancer with a pharmaceutical composition including at least one antisense oligonucleotide in an amount effective to inhibit primary brain cell proliferation. The invention also provides probes and primers useful to identify primary brain cells having amplified and/or rearranged genes encoding c-myb.

17 Claims, 3 Drawing Sheets

OTHER PUBLICATIONS

Venturelli et al., PNAS 87:5963 (1990), Inhibition of T Cell Proliferation by a MYB Antisense Oligomer is Accompanied by Selective Down Regulation of DNA Polymerase Expression.

Welter et al., Cancer Letters 52:57 (1990), The cellular myb oncogene is amplified, rearranged and activated in human glioblastoma cell lines.

Whitesell et al., PNAS 90:4665 (1993), Stability, Clearance, and Disposition of Intraventricularly Administered Oligodeoxynucleotides: Implications for Therapeutic Application within the Central Nervous System.

Anfossi et al., PNAS 86:3379 (1989), An Oligomer Complementary to C–myb–Encoded mRNA Inhibits Proliferation of Human Myeloid leukemia cell lines.

Bacon et al., Oncogene Res. 6:13 (1991), Walking Along Human c–myc mRNA with Antisense Oligodeoxynucleotides: Maximum Efficacy of the 5' Cap Region.

Brelvi et al., J. Cell Physiol. 131:43 (1987), Coordinate Expression of C–myc, C–myb and Histone H4 Genes in Reversibly Differentiating HL60 Cells.

Calabretta et al., Cancer Invest. 11:191 (1993), Functional Significance of C–myb Expression in Normal and Leukemic Hematopoiesis.

Calabretta et al., Ann. of New York Acad. of Sci. 660:117 (1992), Proto–oncogenes in the Regulation of Normal Hematopoiesis: An Antisense Approach.

Chern et al., Blood 78:991 (1991), Induction of Hemoglobin Synthesis by Downregulation of myb Protein with an Antisense Oligodeoxynucleotide.

Yoon Sang Cho–Chung, Antisense oligonucleotides for the treatment of cancer, Current Drugs Ltd ISSN, pp. 1737–1750.

Flores, et al., Society for Neuroscience Abstracts vol. 20:835 (1994), Suppression of Human Medulloblastoma Cell Proliferation with Antisense Oligonucleotides to the C–myb oncogene.

Flores, et al., Neurosurgery 35:575 (1994), Growth Inhibition of Glioma and Medulloblastoma Cells and Down Regulation of Platelet Derived Growth Factor Receptors with Antisense Oligonucleotides to C–myb oncogene.

Gewirtz et al., Ann. of New York Acad. of Sci. 660:178 (1992), Therapeutic Applications of Antisense DNA in the Treatment of Human Leukemia.

Harrison, Lancet 342:254 (1993), Antisense: into the Brain.

Helene, Eur. J. of Cancer 27:1466 (1991), Rational Design of Sequence–specific Oncogene Inhibitors Based on Antisense and Antigene Oligonucleotides.

Laske et al., Neurosurgery 80:520 (1994), Efficacy of Direct Intratumoral Therapy with Targeted Protein Toxins for Solid Human Gliomas in Nude Mice.

Milligan et al., Ann. of New York Acad. of Sci. 716:228 (1994), Development of Antisense Therapeutics: Implications for Cancer Gene Therapy.

Paoletti, Antisense Oligonucleotides as potential antitumor agents: prospective views and preliminary results, AntiCancer Drug Design 2:325 (1988).

Ramsay et al., Cell Growth and Differentiation 3:723 (1992), Myb Expression is Higher in Malignant Human Colonic Carcinoma and Pre–malignant Adenomatous Polyps than in Normal Mucosa.

Ratajczak et al., PNAS 89:11823 (1992) In Vivo Treatment of Human Leukemia in SCID Mouse Model with C–myb Antisense Oligodeoxynucleotides.

Stein et al., Science 261:1004 (1993), Antisense Oligonucleotides as Therapeutic Agents—Is the Bullet really Magical?.

Szczylik et al., Exp. Hem. 20:779 (1992), Inhibition of In Vitro Proliferation of Chronic Myelogenous Leukemia Progenitor Cells by C–myb Antisense Oligonucleotides.

Ullrich et al., Nature 309:14 (1984), Human Epidermal Growth Factor Receptor cDNA Sequence and Aberrant Expression of the Amplified Gene in A431 Epidermoid Carcinoma Cells.

Chronic Myeloid Leukemia: Potential for antisense therapy, Lancet 340:1262 (1992).

ANTISENSE OLIGONUCLEOTIDES AND METHODS FOR TREATING CENTRAL NERVOUS SYSTEM TUMORS

This is a continuation of application Ser. No. 08/437,150, filed May 2, 1995, now abandoned, which is a continuation in part of application Ser. No. 08/383,733, filed Feb. 6, 1995, now abandoned.

BACKGROUND OF THE INVENTION

The work described herein was supported by the National Institute of Health under grant numbers K08-NS-01713 and R01-NS-24464. The government may have certain rights in the invention.

c-myb is a nuclear phosphoprotein involved in the regulation of cell proliferation and differentiation. The expression of the c-myb gene is greatest in cells as they prepare to enter and traverse the G1/S transition phase of the cell cycle. The expression of this gene subsequently decreases as cells terminally differentiate. Recent studies have shown that c-myb binds to specific DNA sequences and transactivates transcription of DNA polymerase-alpha and cdc2, two genes that are critical for DNA synthesis. (Baseraga et al., *Ann. NY Acad. Sci.*, 660:64–69 (1992); Ku et al., *J. Biol. Chem.*, 268:2255–2259 (1993).)

c-myb RNA levels are exceptionally high during the proliferation of immature thymocytes, prostate, and during the development of the central nervous system (CNS). Thompson et al., *Nature*, 319:374 (1986); Thiele et al., *Mol. Cell Biol.* 8:1677 (1988). More recent studies have demonstrated that c-myb expression is required for T-lymphocyte proliferation and the proliferation of intermediate-late myeloid and erythroid progenitors, but less important for early progenitor cell amplification. Caracciolo et al., *J. Clin. Invest.*, 85:55 (1990). In human HL-60 leukemic cells, Brelvi and Studzinski reported that c-myb RNA was elevated in cell populations enriched for S-phase cells. Graser et al., *J. Cell Physiol.*, 131:43 (1987). However, not all cells utilize c-myb protein during the proliferative process, and may use other members of the myb family (e.g., b-myb) to carry out these functions.

c-myb is a cellular homolog of the transforming gene v-myb, found in avian myeloblastosis virus (AVM) and the E26 virus. These avian viruses cause myeloblastic leukemias in chickens and can transform myelomonocytic cells in culture. Furthermore, the oncogenic activation of c-myb in chicken hematopoietic cells and murine myeloid tumor cells has been shown to be associated with 5' and 3' truncations. (Cuddihy et al., *Mol. Cell. Biol.*, 13:3505–3513 (1993).) The human c-myb gene has been found to be altered in human glioblastoma multiforme cell lines. The degree of amplification in four cell lines was 10-fold as determined by densitometry. A rearrangement within the coding region and an enhanced gene activity were also noted. Welter, C. et al., *Cancer Letters*, 52:57 (1990).

Antisense oligonucleotides (AONs) are specific nucleic acid sequences that interfere with the translation of mRNA into protein. The administration of antisense to c-myb has recently been shown to inhibit the proliferation of T-cells and other hematopoietic cells. Venturelli, D. et al., *PNAS*, 87:5963 (1990). In studies of human myeloid leukemia cells, c-myb antisense was found to suppress the proliferation of HL-60, ML-3, KG-1, and KG-1a cell lines while antisense to c-myc or c-fes had no effect. Ferrari et al., *Cell Growth Differ.*, 1:543 (1990).

Antisense oligonucleotide sequences complementary to DNA sequences encoding growth factors have been used in vitro to inhibit the growth of malignant brain tumor cell lines in a few instances. For example, 14-mer phosphorothioate oligodeoxynucleotides targeted against PDGF-A-chain-, -B-chain-, and -bFGF-mRNA, were used to inhibit cell proliferation of two glioblastoma cell lines, HTZ-146 and HTZ-17. Behl, C. et al., *Neurosurgery*, 33:674 (1993). In the A172 glioblastoma cell line, antisense oligonucleotides complementary to c-sis mRNA inhibited cell proliferation in a time- and dose-dependent fashion. The c-sis oncogene encodes the B-polypeptide chain of PDGF. Nitta, T. et al., *Neurosurgery*, 34:309 (1994). The addition of bFGF-specific antisense oligonucleotide to the U87 glioblastoma cell line significantly inhibited the growth rate of these cells within 48 hours and blocked proliferation beyond 2 days. Murphy et al., *Molecular Endocrinology*, 6:877 (1992).

One study has examined the effects of an antisense oligonucleotide to the c-myb oncogene on neuroectodermal tumor cells. Neuroectodermal cell lines give rise to neoplasms that typically originate in the peripheral nervous system and spinal cord, and are not considered to have originated in the brain. In this study, Raschella et al. found that c-myb antisense oligonucleotide down-regulated MYB protein and inhibited the proliferation of neuroectodermal cell lines. Raschella et al., *Cancer Res.*, 52:4221 (1992).

Glioblastoma multiforme is one example of a brain tumor and is often fatal. To this date there are few effective treatments for brain tumors. Current treatment methods such as surgery, radiation therapy, and systemic chemotherapy for malignant brain tumors have not resulted in a significant prolongation in survival. The 2-year survival rate for the most common brain tumor, the glioblastoma multiforme, is less than 20% and disseminated disease in the cerebrospinal fluid has an estimated survival of 3–4 months in adults.

The lack of specificity of conventional chemotherapy for malignant cancers found in the brain has led to dose-limiting side effects and unacceptable toxicity. Because of the limitations of these conventional agents, investigators have sought new innovative treatment modalities. Immunotoxins, toxic proteins covalently linked to a tumor-specific monoclonal antibody or other carrier ligand, are one class of compounds that combine exquisite cell-type selectivity with extraordinary potency.

Thus, there is a need to develop compositions and methods for treating central nervous system tumors including brain tumors utilizing antisense oligonucleotides. There is a need to develop compositions and treatment methods that result in down-regulation and inactivation of c-myb and other cellular products involved in uncontrolled cell proliferation of central nervous system tumor cells.

SUMMARY OF THE INVENTION

The invention includes methods and compositions for treating central nervous system tumors using antisense oligonucleotides. The invention also includes diagnostic methods of identifying patients with tumors for treatment with antisense oligonucleotides.

A method of the invention involves treating central nervous system tumors by administering to a patient a pharmaceutical composition with an effective amount of at least one antisense oligonucleotide that inhibits proliferation or growth of the central nervous system tumor. Central nervous system tumors include those tumors that originate in the brain and have metastasized elsewhere as well as tumors originating elsewhere that have metastasized to the brain and/or central nervous system. Specific examples include those tumors that originate in the brain such as glioma multiforme and medulloblastomas. The pharmaceutical composition preferably includes a carrier and delivery system that provides for delivery that circumvents the blood/brain barrier to tumors located in the brain. The preferred delivery method and route of administration is intratumorly using an implantable device to deliver the pharmaceutical composition.

A pharmaceutical composition includes at least one antisense nucleotide that can inhibit proliferation or growth of central nervous system tumor cells or cell lines. It is preferred that the composition include at least one antisense oligonucleotide that is complementary to and can hybridize to a portion of a mRNA encoding c-myb. The preferred antisense oligonucleotides are complementary to the nucleotide sequence encoding amino acids 2–7 or 182–188 of the c-myb gene product. The antisense oligonucleotides inhibit expression of c-myb in the tumor cells.

The composition can include more than one antisense oligonucleotide and can also include antisense oligonucleotides complementary to DNA sequences encoding growth factor receptors such as EGF receptor and PDGF receptor. A pharmaceutical composition is formed by combining one or more antisense oligonucleotides with a pharmaceutically acceptable carrier in an amount effective to inhibit growth and/or proliferation of central nervous system tumor cells such as cancer cells originating in the brain. The carriers are selected to be compatible with and enhance delivery of antisense oligonucleotides in the delivery method selected. Delivery methods include the use of implantable devices such as indwelling catheters and infusion pumps, liposomes, gels, wafers, foams and the like. The preferred route of administration is intratumorly.

The invention also includes diagnostic methods for identifying central nervous system tumors that have enhanced expression of or alterations in the coding sequence for c-myb. The method of the invention involves measuring the level of c-myb expression in central nervous system cancer cells obtained from surgery or biopsy. Those patients with tumors that have enhanced levels of expression of c-myb are especially suitable for treatment with a pharmaceutical composition including at least one antisense oligonucleotide to c-myb. The methods of detecting enhanced expression include standard methods such as Northern Blot, RT-PCR and the like. Probes are complementary to and hybridize to all or a portion of a nucleotide sequence encoding c-myb. The preferred probes are antisense oligonucleotides that can also serve to inhibit expression of c-myb.

DETAILED DESCRIPTION

Figure 1:
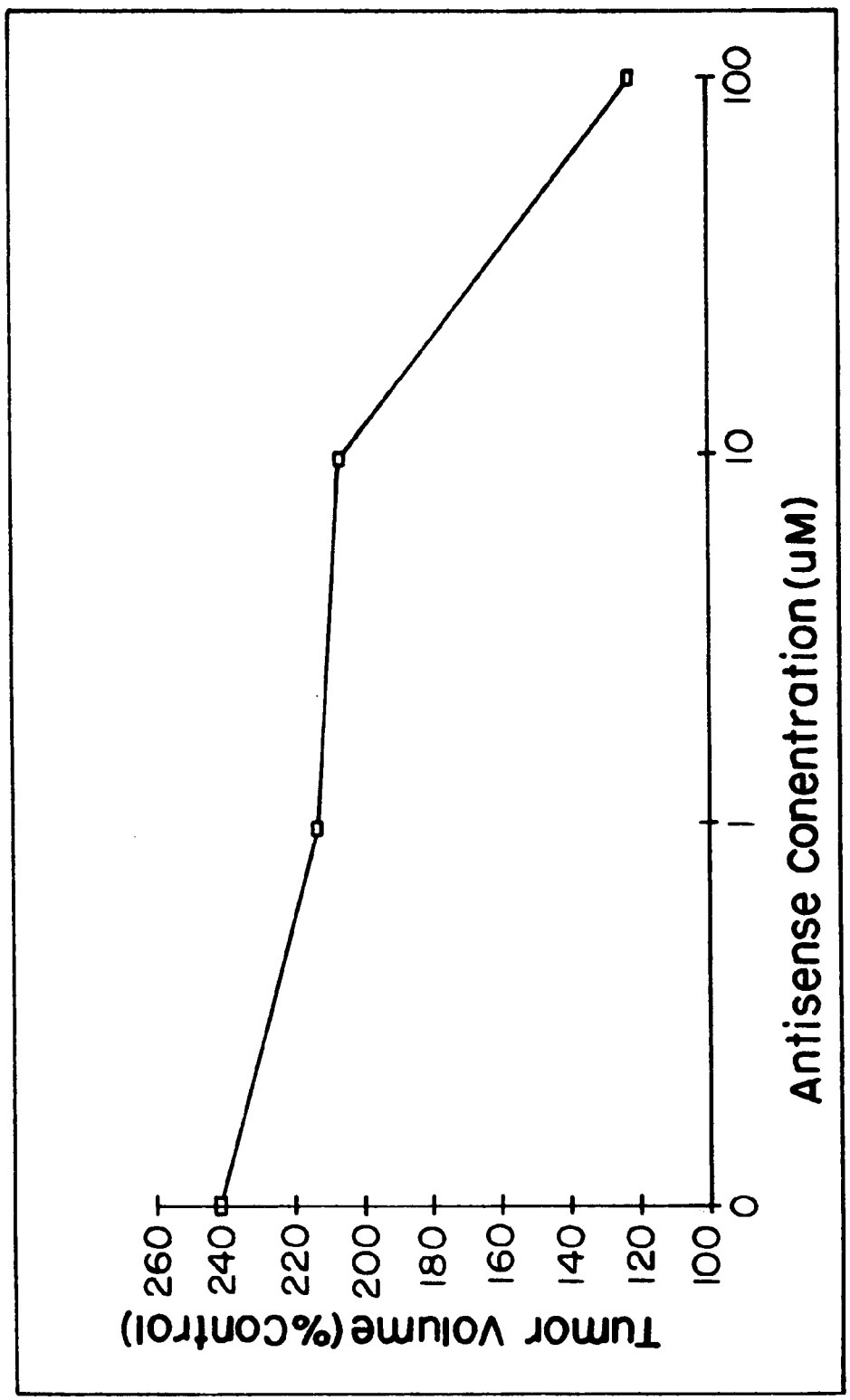
FIG. 1. Effect of dose of AONcmyb(2–7) on intraflank U87 tumors in nude mice.

The invention provides compositions and methods for treating central nervous system tumors. Central nervous system tumors include tumors that originate in the brain as well as tumors that originate elsewhere and metastasize to the brain. The methods are particularly directed toward treatment of tumors found in the brain. The compositions of the invention include at least one antisense oligonucleotide that interferes with the translation of a messenger RNA (mRNA) encoding c-myb. The antisense oligonucleotides inhibit expression of c-myb and/or proliferation of central nervous system tumor cells such as glioblastoma and medulloblastoma tumor cells and cell lines. The antisense oligonucleotides are combined with pharmaceutically acceptable carriers and/or delivery vehicles in an amount effective to suppress tumor cell proliferation to form a pharmaceutical composition. The preferred delivery methods are those utilized to deliver agents to the brain. A method of the invention involves treating patients with a central nervous system tumor such as a cancer that originates in the brain by administering at least one antisense oligonucleotide in a pharmaceutical composition to the patient.

The compositions of the invention are useful to down-regulate expression of c-myb in central nervous system tumors such as brain tumor cells, to inhibit proliferation of central nervous system tumors and/or to treat central nervous system tumors. The antisense oligonucleotide can also be used to form all or a portion of a probe. Probes can be used to detect levels of expression of c-myb in central nervous system tumor and/or brain cancer biopsy specimens. Other probes can also be derived from the c-myb sequence which are complementary to and hybridize to the human c-myb DNA or mRNA sequence but are not antisense. Detection of c-myb oncogene expression in central nervous system tumor biopsy or surgical material may provide a diagnostic and prognostic test for determining the grade of a brain tumor. For example, high-grade, poorly-differentiated glial tumors express c-myb and low-grade astrocytomas do not express this oncogene.

1. Antisense Oligonucleotides

Antisense oligonucleotides are oligonucleotides that are complementary to and can hybridize to a mRNA sequence and inhibit translation of the mRNA sequence. This inhibition of translation results in an inhibition of expression of the gene encoded on the mRNA. The sequences of the antisense nucleotides of the invention are selected to be complementary to and/or hybridize to a portion of the mRNA including c-myb and/or to inhibit expression of c-myb in central nervous system tumors such as brain cancer cells or cell lines or in tumors that have metastasized to the brain. The antisense oligonucleotides preferably also inhibit central nervous system tumor cell proliferation.

The DNA sequence coding for human c-myb has about 1,927 nucleotides and encodes about a 640 amino acid protein. The DNA sequence coding for human c-myb is known and has been published by Majello et al., *Proc. Nat. Acad. Sci.*, 83:9636–9640 (1986). Antisense oligonucleotides can be prepared that are complementary to and hybridize to any portion of the coding sequence as well as portions upstream from the 5' initiation region. However, it was thought that antisense oligonucleotides located downstream from the initiation region and the 5' coding regions encoding about the first 10 amino acids would not effectively inhibit translation because of a read-through effect. In addition, some antisense oligonucleotides selected to hybridize to portions of the c-myb mRNA may not effectively inhibit mRNA translation in central nervous system tumors such as brain cancer cells if there has been rearrangement in the DNA coding sequence of c-myb. Rearrangements including deletions could result in antisense oligonucleotides that, although derived from the known coding sequence, would not bind to mRNA for c-myb in brain tumor cells.

The sequence of the oligonucleotides is selected to be sufficiently complementary to the mRNA sequence coding for c-myb so that the antisense oligonucleotide forms a stable hybrid with c-myb mRNA and inhibits the translation of the mRNA sequence under physiological conditions. It is preferred but not necessary that the antisense nucleotide be 100% complementary to a portion of the c-myb sequence. The antisense oligonucleotide also preferably hybridizes to isolated c-myb mRNA under the following conditions: blots are first incubated in prehybridization solution (5×SSC, 25 mM NaPO4 (pH 6.5), 1×Denhardt's solution, 1% SDS) at 42° C. for at least 2 hours, and then hybridized with radiolabelled cDNA probes or oligonucleotide probes ($1\times10^6$ cpm/ml of hybridization solution) in hybridization buffer (5×SSC, 25 mM NaPO4 (pH 6.5), 1×Denhardt's solution, 250 μg/ml Torula RNA, 50% deionized formamide, 1% SDS, 10% dextran sulfate). Hybridization for 18 hours at 30–42° C. is followed by washing of the filter in 0.1–6× SSc, 0.1% SDS three times at 25–55° C. The hybridization temperatures and stringency of the wash will be determined by the length of the GC content of the oligonucleotides in accord with the guidelines described by Sambrook et al. cited supra.

It is preferred that the antisense oligonucleotide inhibits tumor cell proliferation about 50–100% and/or expression of c-myb in central nervous system tumor cells.

Inhibition of tumor cell proliferation can be measured using a variety of methods known to those of skill in the art. Those methods include $^3$H thymidine assays of cells cultured in vitro, evaluating a change in the size of the tumor per unit/time using CT or MRI scans, measuring the amount of labelling of tumor tissue using an agent such as bromodeoxyuridine.

Specific examples of antisense oligonucleotides that are complementary to and can hybridize to mRNA for c-myb include those that bind to the coding sequence for amino acids 2–7 of the c-myb product encoded by the mRNA. These oligonucleotides are complementary to and can hybridize to the coding sequence at nucleotides 120–137 of the sequence of Majello et al. The antisense oligonucleotides that can hybridize to mRNA region for amino acids 2–7 can have a sequence selected from the group consisting of:

| | |
|---|---|
| 5'-GTG CCG GGG TCT TCG GGC-3' | SEQ ID NO:1 |
| 5'-TG CCG GGG TCT TCG GGC-3' | SEQ ID NO:2 |
| 5'-G CCG GGG TCT TCG GGC-3' | SEQ ID NO:3 |
| 5'-CCG GGG TCT TCG GGC-3' | SEQ ID NO:4 |
| 5'-GTG CCG GGG TCT TCG GG-3' | SEQ ID NO:5 |
| 5'-GTG CCG GGG TCT TCG G-3' | SEQ ID NO:6 |
| 5'-GTG CCG GGG TCT TCG-3' | SEQ ID NO:7 |

The preferred antisense oligonucleotide has a sequence: 5' GTG CCG GGG TCT TCG GGC-3' SEQ ID NO: 1.

Antisense oligonucleotides can also hybridize to mRNA encoding c-myb at the region encoding amino acids 182–188. This region of the c-myb gene product is the DNA binding region and acts to transactivate transcription of other genes such as cdc2, the EGF receptor, and the IGF1 receptor. This region of the mRNA sequence is found at nucleotides 663–684 in the sequence of Majello et al. and is located substantially downstream from the 5' initiation codon. It was surprising that antisense oligonucleotides to DNA sequence encoding amino acids 182–188 could inhibit c-myb expression in brain tumor cells because this region is much farther downstream than the 5' initiation codons and because of the possibility of rearrangements of c-myb coding sequence in brain tumor cells such as gliomas.

Antisense oligonucleotides that are complementary to and can hybridize to the mRNA region coding for amino acids 182–188 can have a sequence selected from the group consisting of:

| | |
|---|---|
| 5'-TGT AGA ATT CCA GTG GTT CTT-3' | SEQ ID NO:8 |
| 5'-GT AGA ATT CCA GTG GTT CTT-3' | SEQ ID NO:9 |
| 5'-T AGA ATT CCA GTG GTT CTT-3' | SEQ ID NO:10 |
| 5'-AGA ATT CCA GTG GTT CTT-3' | SEQ ID NO:11 |
| 5'-GA ATT CCA GTG GTT CTT-3' | SEQ ID NO:12 |
| 5'-A ATT CCA GTG GTT CTT-3' | SEQ ID NO:13 |
| 5'-ATT CCA GTG GTT CTT-3' | SEQ ID NO:14 |
| 5'-TGT AGA ATT CCA GTG GTT CT-3' | SEQ ID NO:15 |
| 5'-TGT AGA ATT CCA GTG GTT C-3' | SEQ ID NO:16 |
| 5'-TGT AGA ATT CCA GTG GTT-3' | SEQ ID NO:17 |
| 5'-TGT AGA ATT CCA GTG GT-3' | SEQ ID NO:18 |
| 5'-TGT AGA ATT CCA GTG G-3' | SEQ ID NO:19 |
| 5'-TGT AGA ATT CCA GTG-3' | SEQ ID NO:20 |

The preferred antisense oligonucleotide that is complementary to and hybridizes to codons 182–188 has a sequence: 5'-TGT-AGA-ATT-CCA-GTG-GTT-CTT-3' SEQ ID NO: 8.

The antisense oligonucleotides are preferably about 12–40 nucleotides long. About 12 nucleotides are desired to ensure that the antisense oligonucleotide can specifically inhibit translation of the c-myb mRNA. Oligonucleotides with more than about 40 nucleotides can have poor uptake into the cells. Preferably, the antisense oligonucleotide has about 15–21 nucleotides.

Antisense oligonucleotides can be synthesized using automated DNA synthesis and standard methods known to those of skill in the art. A preferred method is that described by Iyer et al., *J. Am. Chem. Soc.*, 112:1253 (1990). Antisense oligonucleotides can be synthesized as oligomers of ribonucleotides, deoxyribonucleotides and deoxynucleotides. The antisense oligonucleotides can also be synthesized using chemically modified nucleotides such as the phosphorothioate derivatives. Modifications known to those of skill in the art can be selected to improve cellular uptake and/or in vivo half-life of the antisense oligonucleotides without interfering with the ability of the antisense oligonucleotide to inhibit expression of c-myb. It is especially preferred to select a modified oligonucleotide that decreases nuclease digestion of the oligonucleotide such as the phosphorothioate derivatives.

Antisense oligonucleotides can be isolated and characterized for purity using high pressure liquid chromatography. The preferred antisense oligonucleotides are essentially free of contaminants such as triethyl ammonium acetate, and other residues from the purification process.

Once synthesized and isolated, at least one antisense oligonucleotide is combined with a pharmaceutically acceptable carrier to form a composition. The pharmaceutically acceptable carrier is preferred to be compatible with the mode of delivery selected.

Delivery methods are preferably those that are effective to circumvent the blood-brain barrier and are effective to deliver agents to brain tumors. For example, delivery methods may include the use of liposomes. The composition and formation of liposomes are known to those of skill in the art. Other delivery methods known to those of skill in the art include the use of implantable devices such as pumps, wafers, gels, foams and fibrin clots. Carriers suitable for these delivery methods can be combined with antisense oligonucleotides in suitable formulations. For implantable pumps and the like, the preferred pharmaceutical carriers include Ringer's solution, saline, phosphate buffered saline, dextrose and other physiological salt solutions.

At least one antisense oligonucleotide is combined with a pharmaceutically acceptable carrier in an amount effective to inhibit proliferation of central nervous system tumors such as brain tumor cells or cell lines of about 50–100%, more preferably about 80–100%. Inhibition of tumor cell proliferation or growth can be measured using standard methods. The dose is also preferably selected in a range where minimal toxicity of the normal brain cells is seen. The dosage is selected to achieve maximum inhibition of proliferation of the cells with the minimum amount of toxicity. The dosage ranges for a particular composition can be determined by standard methods such as described in Example 3. Dosage can also be determined by determining the tumor volume using MRI scan. A dosage is then selected to deliver an amount of about 0.5 to 10 nanomoles per 100 $mm^3$ of tumor. The preferred dosage ranges include about 5–10 nmole per 100 $mm^3$–300 $mm^3$ of tumor tissue.

The pharmaceutical composition can include one or more antisense oligonucleotides that inhibit proliferation of central nervous system tumor cells. For example, an antisense oligonucleotide complementary to the region going from amino acids 2–7 and an oligonucleotide complementary to the region coding for amino acids 182–188 can be combined together. Alternatively, antisense oligonucleotides that inhibit expression of c-myb can be combined with antisense oligonucleotides that inhibit expression of growth factor receptors such as the epidermal growth factor receptor (EGF) and the Platelet Derived Growth Factor (PDGF) receptors and the like. It is preferred that about 2 different oligonucleotides be included in a composition to maximize inhibition of brain tumor cell proliferation. It is also preferred that any combination includes an antisense oligonucleotide complementary to the sequence encoding codons 2–7 or an antisense oligonucleotide complementary to codons 182–188 of c-myb.

Methods of Treating Central Nervous System Tumors

The methods of the invention are directed to treating cancers found in the central nervous system especially those located in the brain. Cancers that are located in the brain can be those that originate from brain tissue or those that originate elsewhere and metastasize to the brain. The methods also include treating cancers that originate in the brain but have metastasized or disseminated elsewhere. Treating cancers found in the brain is more difficult and less successful because of the need to select treatments and delivery methodologies that can overcome the blood-brain barrier. The pharmaceutical compositions of the invention are combined with carriers and delivery methods selected to penetrate or circumvent the blood/brain barrier.

Specific non-limiting examples of the central nervous system tumors include those tumors that originate in the brain such as glioblastoma multiforme and medulloblastoma. There are few treatments that are successful with these types of cancer and they are often fatal within one year of diagnosis. These tumors can be diagnosed based upon MRI and CT scans along with symptoms such as headaches, seizures and focal motor weakness.

Tumors that originate elsewhere but that can metastasize to the central nervous system include breast and lung carcinoma. These secondary tumors are often difficult to treat because delivery systems are not often selected to maximize delivery of the chemotherapeutic agent to the central nervous system especially the brain.

Patients diagnosed with a tumor located in the central nervous system are selected for treatment with a composition of the invention. Optionally, patients may be further selected based upon examination of their central nervous system cancer tissue for overexpression of c-myb. Those cancers having about 2–5 fold increase in expression of c-myb as compared with normal brain tissue or central nervous system tissue may be particularly suitable for treatment with the c-myb antisense oligonucleotides. For example, high-grade poorly-differentiated glial tumors express c-myb and low-grade astrocytomas do not express this oncogene.

Patients may be those that have been treated using standard treatment methods. Those standard treatment methods include surgical resection with or without chemotherapy. In this case, the pharmaceutical composition may be administered concurrent with standard chemotherapy or after standard chemotherapy has been terminated.

The pharmaceutical composition is administered to the patient by a variety of routes including parenterally, intravenously, intratumorally, intrathecally and via the CSF. The route of administration for treating patients with tumors located in the brain is selected to circumvent the blood/brain barrier. The preferred method for treating tumors located in the brain is to utilize an implantable device such as an indwelling catheter through which the antisense oligonucleotides can be infused directly into the tumor. For treating disseminated tumors such as those in the cerebrospinal fluid, the pharmaceutical composition is administered to the CSF.

Delivery systems and carriers are selected to maximize delivery to tumor tissue in the central nervous system especially in the brain. Such delivery systems and carriers are known to those of skill in the art. These delivery systems include liposomes, foams, wafers, gels and fibrin clots and the like. Delivery systems also include implantable devices such as indwelling catheters and infusion pumps. The delivery method can be selected depending on the location and type of tumor.

The pharmaceutical composition is preferably administered in an amount effective to inhibit tumor cell growth by about 50–100%, preferably 80–100%. It is preferred that the amount administered is an amount effective to maximize inhibition of tumor cell proliferation while minimizing toxicity. The dosage can vary depending on the size of the tumor, the location of the tumor, the route of administration, the delivery mode, whether treatment is localized or systemic, and whether the treatment is being used in conjunction with other treatment methodologies. Inhibition of glioma and medulloblastoma tumors can be seen with about 5–10 nmoles of antisense oligonucleotides per 300 $mm^3$ of tumor volume when delivered intratumorally. Concentrations of about 0.5 to about 10 nanomoles/100 $mm^3$ tumor volume may be employed. Dosages can be determined using standard methodologies as in Example 3. Preferably a dosage is determined by determining tumor volume using a MRI scan and then selecting a dose that encompasses that tumor volume. Those skilled in the art can determine appropriate dosages and schedules of administration depending on the situation of the patient.

The composition is preferably administered continuously until inhibition of tumor growth or tumor regression is observed. Tumor size or reoccurrence can be monitored using MRI or CT scanners. Preferably the composition is administered about 2 days up to a year. Advantageously, the time of administration can be coupled with other treatment methodologies. The antisense treatment may be applied before, after, or in combination with other treatments such as surgery, chemotherapy, or radiation. Continued inhibition of tumor growth or tumor regression can be monitored using MRI or CT scans to ensure that the tumor has not begun to grow again either locally or at metastatic sites. The length of time of administration can be varied depending on the treatment combination selected and evidence of continued inhibition of tumor growth or tumor regression.

Administration of antisense oligonucleotides to c-myb to inhibit growth of brain tumors has been examined by examining the effect of antisense oligonucleotides on the growth of the U87 glioblastoma cell line. The U87 glioblastoma cell line is a very aggressive grade 3 human glioblastoma. Growth of the U87 cell line is inhibited in vitro by administration of antisense oligonucleotides to codons 2–7 and codons 182–188 of c-myb. See Table 1. The antisense oligonucleotides also inhibit growth of U87 tumors in the flanks of rats when the antisense oligonucleotides are administered directly to the tumor tissue. See FIGS. 1 and 2. An antisense oligonucleotide complementary to codons 2–7 of human c-myb can also prolong survival of rodents with U87 intrastriatal brain tumors when it is infused into the brain tissue. See FIG. 3. Antisense oligonucleotides to c-myb are effective to inhibit growth of primary brain cancer both in vivo and in vitro.

Antisense oligonucleotides can be examined for dose response in both rodent and primate species as described in Example 3. Inhibition of tumor growth as measured by examining tumor size or an increase in survival time can be used to determine effectiveness of the dose administered. A series of different doses will be administered using a continuous infusion pump such as the Alzet Osmotic Minipump (Alza, Palo Alto, Calif.). The dose range will be from 0.1 nanomole/hour up to 3 nanomole/hour as described in Example 4. The effect on of different doses on tumor size and/or survival time will be evaluated in primates and rodents injected with U87 tumor cells.

Indications of toxicity in normal tissues due to administration of antisense oligonucleotides can also be monitored. Animals receiving different doses of the antisense oligonucleotides will be examined for toxic effects on normal brain and other tissues using standard techniques. Tissues from treated animals will be examined for evidence of cell death or other cell damage. An $LD_{50}$ can be determined using standard methodology.

In a preferred version, a patient having glioma multiforme is treated with pharmaceutical composition including at least one antisense oligonucleotide complementary to a nucleotide sequence of c-myb encoding amino acids 182 to 188 or amino acids 2 to 7 in physiological saline. Preferably, the patient is treated with antisense oligonucleotides after conventional surgical resection and chemotherapy. The composition is administered using an implantable slow infusion pump. The device is designed to administer the pharmaceutical composition by convection-enhanced infusion. The patient will be treated until there is radiographic or clinical evidence of inhibition of tumor growth or regression.

Methods of Diagnosis

The invention also provides for probes and methods of using probes and diagnostic assays. The probes of the invention are complementary to and hybridize to all or a portion of a sequence encoding human c-myb. The probe can be designed to hybridize to mRNA or DNA and is preferably detectably labeled. When expression levels are to be quantitated, it is preferred that the probe hybridizes to mRNA. The method of the invention involves contacting mRNA from a cell type or within a cell with a probe that hybridizes to all or a portion of a sequence encoding human c-myb to form hybrids, and detecting and/or quantitating the amount of the sequence encoding c-myb by detecting and/or quantitating the amount of hybrids formed.

The probes and the methods of the invention are useful to identify central nervous system tumor cells such as brain cancer cells in which c-myb is overexpressed and/or in which the sequence for c-myb has undergone a rearrangement such as amplification or deletions. Detection of central nervous system or brain cancer cells having an overexpression of c-myb and/or rearrangement of c-myb gene sequence can be used to select patients for treatment with antisense oligonucleotides specific for c-myb.

The probes of the invention are complementary to and hybridize to all or a portion of DNA or RNA sequences encoding c-myb. The preferred probes are complementary to and hybridize to a sequence encoding amino acids 2 through 7 or the sequence encoding amino acids 182 to 188 of human c-myb and are antisense oligonucleotides. The probes hybridize to c-myb mRNA under standard Northern blot conditions performed as described (Sambrook et al., 1989, Sambrook, J., Fritsch EF, Maniatis T. Molecular cloning: a laboratory manual. Second edition. Cold Spring Harbor Laboratory Press, Cold Spring Harbor, N.Y.) with some modifications. Briefly, 20 µg of total cellular RNA is denatured 15 minutes at 55° C. in a 1×MOPS, 50% formamide, 6.5% formaldehyde, 100 µg/ml ethidium bromide solution, and then applied to formaldehyde-agarose denaturing gels (1×MOPS, 6.5% formaldehyde, 1% agarose). RNA ladder (BRL) is denatured in the same way and run in parallel for molecular weight determinations. After electrophoresis, RNA is capillary transferred to S&S Nytran (Schleicher & Schuell) for at least 18 hours. The blot is washed briefly in 5×SSC and then baked at 80° C. for 90 minutes.

Hybridization is performed as follows. Blots are first incubated in prehybridization solution (5×SSC, 25 mM NaPO4 (pH 6.5), 1×Denhardt's solution, 1% SDS) at 42° C. for at least 2 hours, and then hybridized with radiolabelled cDNA probes or oligonucleotide probes ($1\times10^6$ cpm/ml of hybridization solution) in hybridization buffer (5×SSC, 25 mM NaPO4 (pH 6.5), 1×Denhardt's solution, 250 µg/ml Torula RNA, 50% deionized formamide, 1% SDS, 10% dextran sulfate). Hybridization for 18 hours at 30–42° C. is followed by washing of the filter in 0.1–6×SSc, 0.1% SDS three times at 25–55° C. The hybridization temperatures and stringency of the wash will be determined by the length of the GC content of the probes in accord with the guidelines described by Sambrook et al. cited supra.

Probes of the inventions can include the following sequences: 5'-GTG CCG GGG TCT TCG GGC-3' SEQ ID NO: 1 or 5'-TGT AGA ATT CCA GTG GTT CTT-3' SEQ ID NO: 8. Probes of the invention can also have the following sequences:

```
5'-GTG CCG GGG TCT TCG GGC-3'      SEQ ID NO:1

5'-TG CCG GGG TCT TCG GGC-3'       SEQ ID NO:2

5'-G CCG GGG TCT TCG GGC-3'        SEQ ID NO:3

5'-CCG GGG TCT TCG GGC-3'          SEQ ID NO:4
```

```
                       -continued
5'-GTG CCG GGG TCT TCG GG-3'            SEQ ID NO:5

5'-GTG CCG GGG TCT TCG G-3'             SEQ ID NO:6

5'-GTG CCG GGG TCT TCG-3'               SEQ ID NO:7
```

Probes are preferably about 17 to 25 nucleotides long. About 17 nucleotides are necessary to provide for specificity of hybridization. Probes can be as large as the entire gene. Probes are preferably about 17 to 25 nucleotides long and include sequences complementary to sequences encoding amino acids 2 through 7 or amino acids 182 to 188 of human c-myb and are antisense oligonucleotides.

The probes are preferably about 100% complementary to the sequence encoding c-myb. However, it is known to those of skill in the art, some mismatches can be present in a probe while still achieving specific hybridization to a sequence encoding c-myb. In a sequence of about 17 to 25 nucleotides about 1 to 3 mismatches can be present. Hybridization conditions can be adjusted in accord with known principals as described in Maniatis, a Guide to Molecular Cloning: A Laboratory Manual, Cold Spring Harbor, New York (1989) to achieve specific hybridization.

The probes are preferably detectably labelled using methods known to those of skill in the art including nick translation, random priming and terminal transferase reactions. Detectable labels include radioactive isotopes, fluorescently labelled tags, biotin and the like. Methods and reagents for labelling probes have been described in Maniatis et al. cited supra.

Probes that are less than about 25 nucleotides can be prepared by automated DNA synthesis. Larger probes can be prepared by methods involving subcloning of restriction fragments. The restriction map and suitable fragments can be derived based upon the known DNA sequence encoding c-myb. Majello et al., *Proc. Nat. Acad. Sci.*, 83:9636–9640 (1986).

The probes of the invention are useful in methods to detect the over expression of c-myb mRNA and the rearrangement of DNA encoding c-myb. A method for detecting over expression of c-myb mRNA includes the following steps:

1. mRNA is isolated from the tissue samples such as central nervous system cancer biopsy tissue;
2. The mRNA is hybridized with the probes specific for c-myb; and
3. Hybrids formed are quantitated.

The preferred standard assay utilizes a northern blot assay in which mRNA is separated by electrophoresis and then hybridized with the radiolabelled probe. The amount of the probe hybridized can be determined using standard densitometry. Alternatively, the hybridization can be conducted on cells in situ using methods known to those of skill in the art. The amount of radiolabelled probe that hybridizes can be quantitated by comparing the number of radiolabelled grains present in individual cells with the amount of radiolabelled grains present in control cells.

In another alternative version, mRNA from primary brain tumor cells can be isolated, reverse transcribed and amplified using one or more of the following primers: 5'-GTG CCG GGG TCT TCG GGC-3' SEQ ID NO: 1, 5'-TGT AGA ATT CCA GTG GTT CTT-3' SEQ ID NO: 8. Other primers specific for human c-myb can be selected and designed using commercially available software. The methods for reverse transcriptase-PCR are known to those of skill in the art and are described in Maniatis et al., cited supra. The amplification products are then detected and quantitated. In a preferred version, amplification products are separated by electrophoreses and detected with a radiolabelled probe. The amplified products are quantitated using standard densitometry.

Overexpression of c-myb mRNA can be detected by detecting an increase in the amount of the radiolabelled probe bound to hybrids. This increase is about 2 to 5-fold over control adult central nervous system tissue. Cancer cells originating in the brain or other central nervous system cancers exhibiting an overexpression of mRNA encoding c-myb are selected as candidates for treatment with antisense oligonucleotides specific for c-myb.

In a preferred version, primary brain cancer cells such as glioma multiforme cells are obtained and mRNA isolated from these cells using standard procedures. Northern blot is performed using a radiolabelled probe having a sequence complementary to DNA sequence encoding amino acids 182 to 188 of c-myb. Expression levels of c-myb-mRNA are determined. Patients with tumors exhibiting about a 2 to 5 fold increase in expression are particularly suitable for treatment using antisense oligonucleotides to c-myb.

In another method of the invention, rearrangements in a DNA sequence encoding c-myb can be detected in cells, preferably the central nervous system or brain cancer cells obtained from surgery or biopsy. The rearrangements of DNA sequence can include amplification of all or part of the gene, truncations at the 5' and 3' ends, deletions and mutations in the DNA sequence that can result in a change in the restriction enzyme map. The steps of the method involve digesting a human DNA sample obtained from central nervous system tissue cancer cells with at least one restriction enzyme that cuts the c-myb DNA sequence, separating the digested fragments, and then hybridizing the fragments to a probe specific for c-myb. The hybrids formed are then quantitated and evaluated for the size of the fragments detected. The amount of hybridization can be quantitated using scanning densitometry. The preferred assay is a standard southern blot assay and methods for performing a southern blot assay are known to those of skill in the art.

Amplification events can be detected when restriction pattern is the same as the control primary brain cancer cells but at least about three-fold more of the radiolabelled hybrids are detected. Rearrangements are detected when the pattern of the size of the fragment changes from that observed in control brain tissue. Brain cancer cells having amplifications are good candidates for treatment with antisense oligonucleotides specific for c-myb. Brain cells having rearrangements can be screened to ensure that the antisense oligonucleotides specific for c-myb can hybridize to the rearranged DNA or mRNA sequence.

All publications and patents are herein incorporated by reference to the same extent as if each individual publication or patent was specifically and individually indicated by reference.

It will be apparent to one of ordinary skill in the art that many changes and modifications can be made in the invention without departing from the spirit or scope of the appended claims.

EXAMPLE 1

Effect of Antisense Oligonucleotides to c-myb oncogene on Cell Proliferation of Glioblastoma and Medulloblastoma Cell Lines The effects of c-myb antisense on human malignant glioblastoma-derived and medulloblastoma-derived tissue-culture cells was examined. Two antisense oligonucleotides to c-myb were selected and evaluated: antisense to the initiator region (AONcmyb(2–7)) and antisense to the transactivation domain (AONcmyb(182–188)).

The antisense nucleotides were selected for the ability to down-regulate expression of c-myb. The coding sequence for c-myb has 1917 nucleotides as described by Majello, cited supra. Antisense for codons 2–7 was selected because this region is adjacent to the start codon for the synthesis of the gene product. Antisense for codons 182–188 was selected because they encode a region of amino acids involved in DNA binding to transactivate transcription. Antisense oligonucleotides selected and evaluated have the following sequence:

(AONcmyb(2–7)) 5'-GTG CCG GGG TCT TCG GGC-3' SEQ ID NO: 1

(AONcmyb(182–188)) 5'-TGT AGA ATT CCA GTG GTT CTT-3' SEQ ID NO: 8.

Antisense oligonucleotides were synthesized as follows. The synthesis of the phosphorothioate antisense oligonucleotides to c-myb follows the protocol of Stec et al., J. Am. Chem. Soc. 106:6077 (1984) as modified by Iyer et al., J. Am. Chem. Soc. 112:1253 (1990). The synthesis employs 1H-tetrazole-catalyzed coupling of phosphoramidites to give phosphite intermediates for conversion to phosphates by oxidation. Reaction of phosphite intermediates with either sulfur ($S_8$) in 2,6-lutidine (0.4 M) or KSeCN in $CH_3CN$ (0.1 M) yields the phosphate moieties.

Antisense oligonucleotides were incubated with glioblastoma (T98, U87, U373) and medulloblastoma (DAOY) cell lines when they were approximately 60% confluent. Antisense oligonucleotides were added at 5 nanomoles/500 microliters and incubated for 2 days in phosphate buffered saline. Growth of cells lines was measured at 2 days using a standard $^3H$-thymidine assay. Coligan et al., *Current Protocols in Immunology*, Vol. 2, pg. A.38 (1992). The results are shown in Tables 1–4.

TABLE 1

Effects of c-myb antisense on U87 cell proliferation.

|  | | Sample size | % Control |
|---|---|---|---|
| Control | 377,831 ± 43,145 | (8) | |
| AONcmyb (2–7) | 74,688 ± 10,145 | (8) | 20%* |
| AONcmyb (182–188) | 92,968 ± 37,259 | (8) | 25%* |
| c-myb (182–188) | 431,558 ± 29,444 | (8) | 114% |

*$p < 0.05$; values represent mean ± SEM in dpm for 3H-thymidine incorporation.

TABLE 2

Effects of c-myb antisense on T98 cell proliferation.

|  | | Sample size | % Control |
|---|---|---|---|
| Control | 128,085 ± 16,254 | (8) | |
| AONcmyb (2–7) | 67,318 ± 6,183 | (6) | 53%* |
| AONcmyb (182–188) | 78,457 ± 3,224 | (6) | 61%* |
| c-myb (182–188) | 108,706 ± 12,149 | (6) | 85% |

*$p < 0.05$; values represent mean ± SEM in dpm for 3H-thymidine incorporation.

TABLE 3

Effects of c-myb antisense on U373 cell proliferation.

|  | | Sample size | % Control |
|---|---|---|---|
| Control | 769,500 ± 31,048 | (8) | |
| AONcmyb (2–7) | 402,504 ± 49,647 | (6) | 52%* |
| AONcmyb (182–188) | 588,082 ± 25,836 | (6) | 76%* |
| c-myb (182–188) | 902,466 ± 45,690 | (6) | 117%* |

*$p < 0.05$; values represent mean ± SEM in dpm for 3H-thymidine incorporation.

TABLE 4

Effects of c-myb antisense on DAOY cell proliferation.

|  | | Sample size | % Control |
|---|---|---|---|
| Control | 1,139,416 ± 81,431 | (12) | |
| AONcmyb (2–7) | 604,061 ± 59,989 | (12) | 53%* |
| AONcmyb (182–188) | 517,725 ± 105,450 | (8) | 45%* |
| c-myb (182–188) | 995,908 ± 118,359 | (8) | 87% |

*$p < 0.05$; values represent mean ± SEM in dpm for 3H-thymidine incorporation.

After 48 hours of incubation, mean proliferation of cell lines in the presence of antisense oligonucleotides to AONcmyb(2–7) was 20% of controls for U87, 52% for U373, 53% for T98, and 53% for DAOY cells (Tables 1–4). All were significant at $p<0.05$. Proliferation of cell lines in the presence of AONcmyb(182–188) was 25% of controls for U87, 76% for U373, 61% for T98, and 45% for DAOY cells (Tables 1–4). These results were also significant at $p<0.05$.

The results show that the addition of antisense oligonucleotides to the initiation region (AONcmyb(2–7)) or to the transactivation domain of c-myb (AONcmyb(182–188)) resulted in a consistent and reproducible inhibition of growth in three glioblastoma cell lines (T98, U87, and U373) and in one medulloblastoma cell line (DAOY). Initial effects of growth suppression were evident as early as 6 hours after the addition of AONs, and cumulative inhibition of growth was demonstrated with daily addition of AONs to the growth medium for 5 days. Suppressive nontoxic doses were in the 100 nanomoles/ml range. Toxicity, measured as 50% or more cells becoming trypan blue positive, was seen at doses greater than 200 nmole/ml.

The results indicate that down-regulation of c-myb results in a suppression of proliferation of glioblastoma and medulloblastoma cell lines. Antisense oligonucleotides to the transactivation region of c-myb (AONcmyb(182–188)) was as effective as antisense oligonucleotide to the initiation region (AONcmyb(2–7)) in suppressing cell proliferation.

EXAMPLE 2

Effects of c-myb AONs on EGF and PDGF Receptor Expression

The effects of c-myb antisense on the expression of epidermal growth factor (EGF) receptors in T98 and U87 cells in vitro was examined using a flow cytometric approach to quantify fluorescently labeled receptors. T98 and U87 cell lines that were treated with 10 $\mu$M antisense oligonucleotides for 48 hours were harvested. About $10^5 10^6$ (number of cells) were incubated with fluorescently labeled antibody to EGF receptor (available from Upstate Biotech, Inc.) for 24 hours. The cells were then analyzed using a Beckman FACS cell sorter.

Platelet derived growth factor (PDGF) receptors on cells treated with antisense as described above were also examined. Antibodies to PDGF receptor were obtained from Upstate Biotech, Inc.

Cells for receptor expression assays were harvested, washed twice in PBS and fixed in 70% ethanol of 2% paraformaldehyde. After washing, cells were incubated with appropriate concentrations of specific receptor antibodies for 2–12 hours. Antibody conjugated FITC was then added to the cell suspensions. Cells were washed well between steps and resuspended in Hanks balanced salt solution, 1% sodium azide, and 1% bovine serum albumin. FITC fluorescence was then assayed by flow cytometry counting 10,000 cells per sample. The amount of fluorescently labeled EGF receptor and PDGF receptor were determined by standard flow cytometry analysis.

Administration of AONcmyb(2–7) resulted in a down-regulation of the EGF receptor binding to 13%–30% control levels in these cell lines. Antisense to the transactivation domain resulted in a down-regulation of binding to 30%–35% of controls (data not shown). The administration of c-myb sense had no effects on EGF receptor binding in comparison to controls. The PDGF receptors were also markedly down regulated. These results suggest that the inhibition of cell proliferation by c-myb antisense may be mediated by the down-regulation of growth factor receptors.

EXAMPLE 3

Effects of AON on Intraflank U87 Tumors in Nude Mice

Solid U87 gliomas were established in the flanks of athymic nude mice aged 4–6 weeks. Each animal received $5 \times 10^6$ U87 cells in 200 µl of medium. The cells were injected subcutaneously into one flank through a 25-gauge needle attached to a tuberculin syringe.

Cells were initially grown in a monolayer at 37° C. in DMEM medium containing 10% fetal calf serum, 2 mM glutamine, 1000 IU/ml of penicillin, and 100 µg/ml of streptomycin. Cells were harvested from culture flasks using trypsin immediately before injection and were kept on ice until the time of injection. Before injection the number of viable cells were confirmed by trypan blue exclusion. Past experience has shown that approximately 90% of tumors will successfully grow in the flank after U87 cell inoculation.

Tumors were allowed to grow for 14 days. Tumor size was evaluated with Vernier calipers using the formula ½ length(width)$^2$ where the length was the longest dimension and the width was the diameter perpendicular to the length. AONcmyb(2–7) was then injected using a Hamilton syringe directly into the tumor at a concentration of 0, 1, 10, or 100 µM in 50 µl volumes on alternate days for 8 days (FIG. 1). At the end of this time period, it was found that the 100 µM concentration was most effective in suppressing tumor growth.

Figure 2:
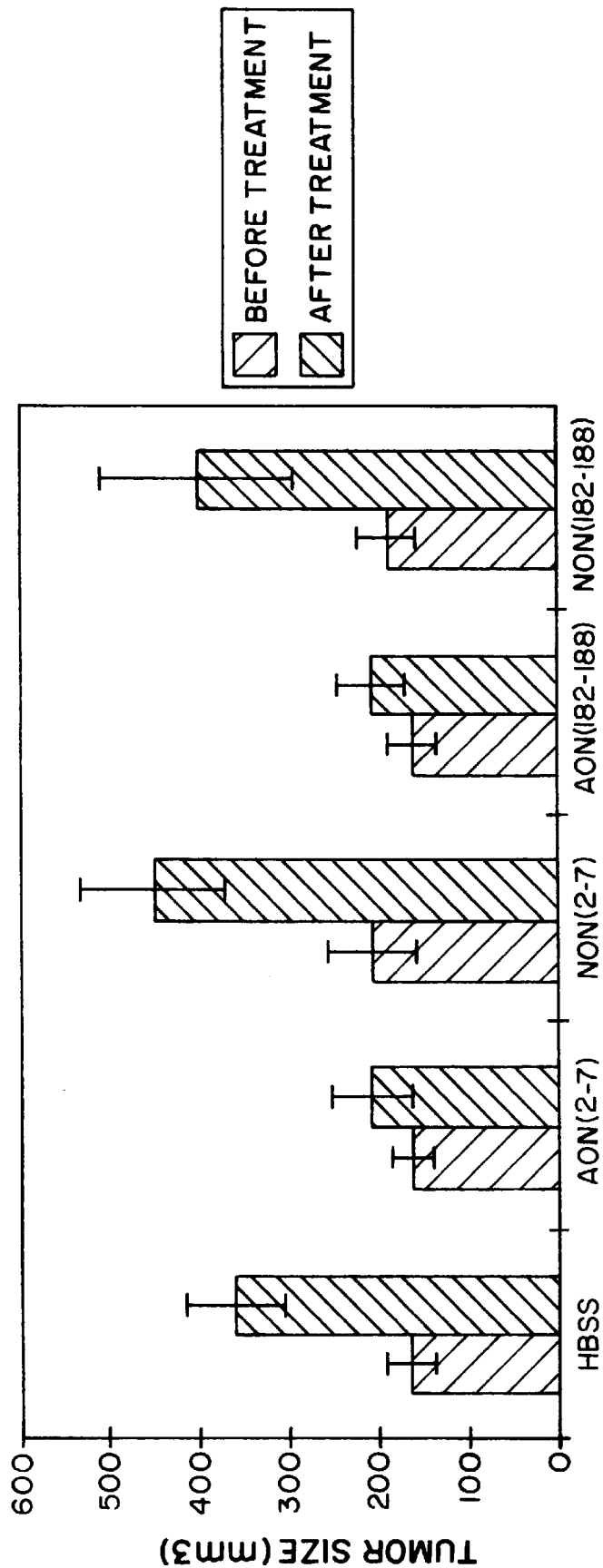
FIG. 2. Effect of AONcmyb(2–7) and AONcmyb (182–188) on U87 tumor growth in the flank of nude mice. Values represent mean±SEM for tumor size in mm$^3$.

The effects of administering 100 µM concentrations of AONcmyb(2–7) and AONcmyb(182–188) with their corresponding nonsense oligonucleotides, NONcmyb(2–7) and NONcmyb(182–188) along with Hank's Balanced Salt Solution as controls was compared. From days 13 to 21 animals received 50 µl(5 nanomoles/injection) injections intratumorally of either antisense, nonsense, or HBSS every two days. At day 21, animals receiving HBSS or nonsense exhibited significant increases in tumor size while those receiving antisense displayed no significant change (FIG. 2). These results show that antisense oligonucleotides administered in vivo inhibited tumor growth.

EXAMPLE 4

Effect of Intracerebral Infusions of c-myb Antisense Oligonucleotides on Tumors in the Brain The effects of infusing c-myb antisense to codons 2–7 on the survival of nude rats with intrastriatal xenografts of human U87 glioblastoma cells was examined. A dose of 0.1 nmole/hour was infused. This dose is equivalent to the delivery of 100 UM of c-myb antisense injected directly into intraflank U87 tumors in 50 Ul volumes on alternate days. Animals received continuous infusions of either c-myb antisense or saline by Alzet Osmotic Minipump (Alza, Palo Alto, Calif.) over a period of 14 days. The pump was implanted immediately above the site of the tumor.

Figure 3:
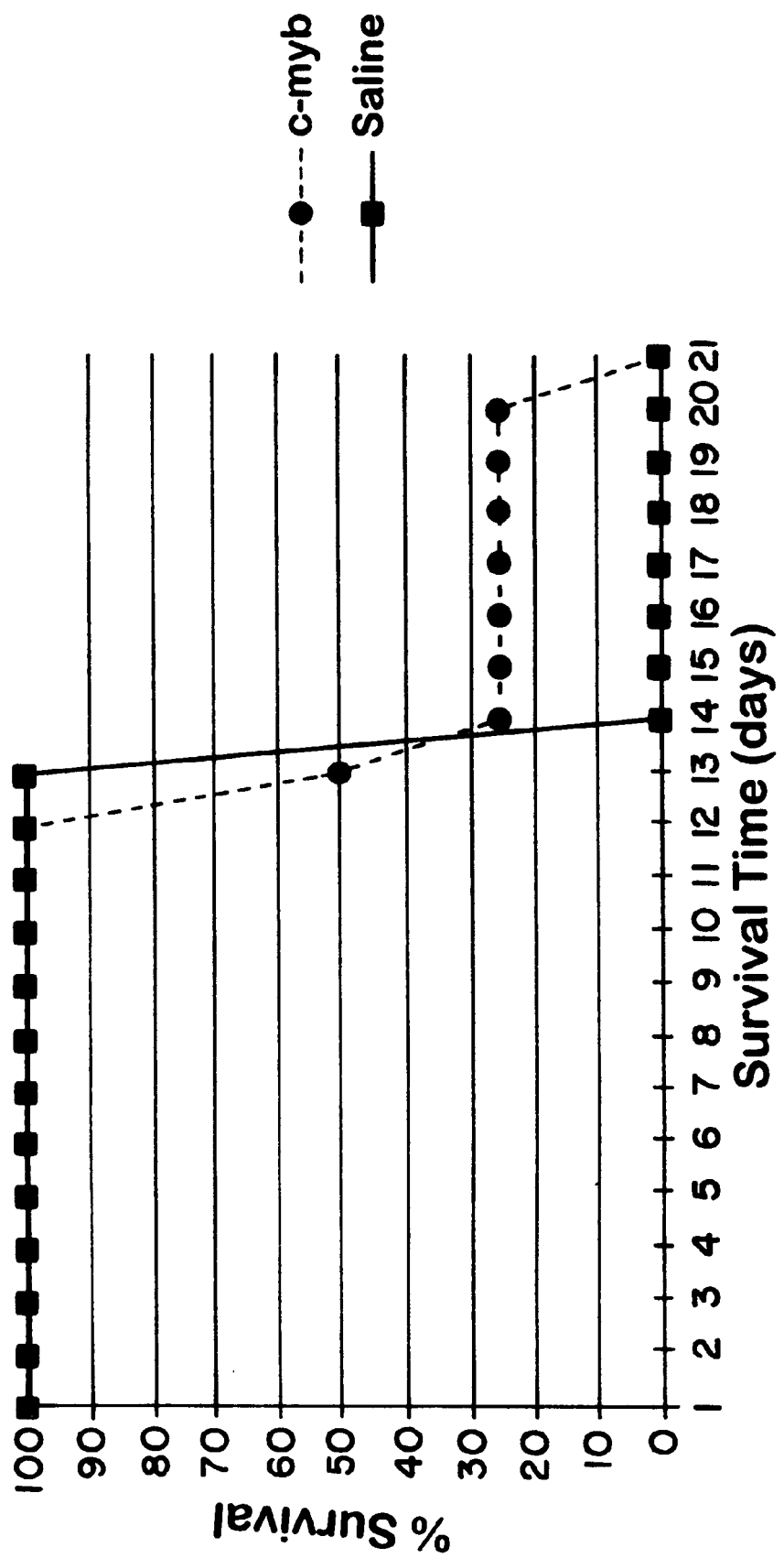
FIG. 3. Effect of intracerebral infusion of c-myb antisense on the survival of nude rats with intrastriatal xenografts of human U87 brain tumors.

The results are shown in FIG. 3. All animals with saline infusions survived for only 13 days after the implantation of the tumor cells (see FIG. 3). In contrast, 25% of the animals with c-myb antisense had increased survival times.

In a study assessing the toxicity of intraventricular antisense administration (Whitesell et al., *Proc. Natl. Acad. Sci.*, 90:4665–4669, 1993), it was determined that dosages of 1.5 nmoles/hr were well tolerated in rats while a dose of 3.0 nmole/hr was toxic. These data suggest that the 0.1 nmole/hr of c-myb antisense used herein to demonstrate efficacy is 30 times below the toxic level for antisense administration in the brain. Therefore, it is believed that an increase in dose of the c-myb antisense can be administered that will improve survival without toxic side effects.

---

---

It is claimed:

1. A method for treating central nervous system cancer comprising administering to a patient with central nervous system cancer at least one antisense oligonucleotide comprising about 15–21 nucleotides, wherein the at least one antisense oligonucleotide hybridizes to an mRNA sequence coding for amino acids 182–188 of human c-myb.

2. A method according to claim 1 wherein the oligonucleotide has the sequence selected from the group consisting of:

| Sequence | SEQ ID |
|---|---|
| 5'-TGT AGA ATT CCA GTG GTT CTT-3' | SEQ ID NO:8 |
| 5'-GT AGA ATT CCA GTG GTT CTT-3' | SEQ ID NO:9 |
| 5'-T AGA ATT CCA GTG GTT CTT-3' | SEQ ID NO:10 |
| 5'-AGA ATT CCA GTG GTT CTT-3' | SEQ ID NO:11 |
| 5'-GA ATT CCA GTG GTT CTT-3' | SEQ ID NO:12 |
| 5'-A ATT CCA GTG GTT CTT-3' | SEQ ID NO:13 |
| 5'-ATT CCA GTG GTT CTT-3' | SEQ ID NO:14 |
| 5'-TGT AGA ATT CCA GTG GTT CT-3' | SEQ ID NO:15 |
| 5'-TGT AGA ATT CCA GTG GTT C-3' | SEQ ID NO:16 |
| 5'-TGT AGA ATT CCA GTG GTT-3' | SEQ ID NO:17 |
| 5'-TGT AGA ATT CCA GTG GT-3' | SEQ ID NO:18 |
| 5'-TGT AGA ATT CCA GTG G-3' | SEQ ID NO:19 |
| 5'-TGT AGA ATT CCA GTG-3' | SEQ ID NO:20. |

3. A method, according to claim 2, wherein the oligonucleotide includes the sequence: 5'-TGT-AGA-ATT-CCA-GTG-GTT-CTT-3' SEQ ID NO:8.

4. A method according to claim 1, wherein the oligonucleotide is administered using an infusion pump.

5. A method according to claim 1, wherein the patient has cancer originating in the brain.

6. A method according to claim 1, wherein the patient has glioma multiforme.

7. The method of claim 1, wherein said central nervous system cancer comprises medulloblastoma.

8. A method for treating central nervous system cancer comprising administering to a patient with central nervous system cancer at least one antisense oligonucleotide comprising about 15–21 nuceotides, wherein the at least one antisense oligonucleotide hybridizes to an mRNA sequence coding for amino acids 2–7 of human c-myb.

9. A method according to claim 8 wherein the antisense oligonucleotide has a sequence selected from the group consisting of:

```
5'-GTG CCG GGG TCT TCG GGC-3'      SEQ ID NO:1
5'-TG CCG GGG TCT TCG GGC-3'       SEQ ID NO:2
5'-G CCG GGG TCT TCG GGC-3'        SEQ ID NO:3
5'-CCG GGG TCT TCG GGC-3'          SEQ ID NO:4
5'-GTG CCG GGG TCT TCG GG-3'       SEQ ID NO:5
5'-GTG CCG GGG TCT TCG G-3'        SEQ ID NO:6
5'-GTG CCG GGG TCT TCG-3'          SEQ ID NO:7.
```

10. A method for inhibiting the growth of CNS tumor cells expressing c-myb, comprising: administering to the cells an antisense oligonucleotide about 15–21 nucleotides in length that hybridizes to an mRNA sequence coding for amino acids 2–7 or 182–188 of human c-myb.

11. A pharmaceutical composition comprising at least one antisense oligonucleotide in admixture with a pharmaceutically acceptable carrier, wherein said at least one antisense oligonucleotide comprising about 15–21 nucleotides hybridizes to a sequence of mRNA coding for amino acids 182–188 of human c-myb, and wherein said oligonucleotide inhibits proliferation of central nervous system cancer cells.

12. A pharmaceutical composition according to claim 1 wherein the oligonucleotide has the following sequence selected from the group consisting of:

```
5'-TGT AGA ATT CCA GTG GTT CTT-3'     SEQ ID NO:8
5'-GT AGA ATT CCA GTG GTT CTT-3'      SEQ ID NO:9
5'-T AGA ATT CCA GTG GTT CTT-3'       SEQ ID NO:10
5'-AGA ATT CCA GTG GTT CTT-3'         SEQ ID NO:11
5'-GA ATT CCA GTG GTT CTT-3'          SEQ ID NO:12
5'-A ATT CCA GTG GTT CTT-3'           SEQ ID NO:13
5'-ATT CCA GTG GTT CTT-3'             SEQ ID NO:14
5'-TGT AGA ATT CCA GTG GTT CT-3'      SEQ ID NO:15
5'-TGT AGA ATT CCA GTG GTT C-3'       SEQ ID NO:16
5'-TGT AGA ATT CCA GTG GTT-3'         SEQ ID NO:17
5'-TGT AGA ATT CCA GTG GT-3'          SEQ ID NO:18
5'-TGT AGA ATT CCA GTG G-3'           SEQ ID NO:19
5'-TGT AGA ATT CCA GTG-3'             SEQ ID NO:20.
```

13. An oligonucleotide about 15–21 nucleotides in length comprising an antisense sequence complimentary to a sequence of mRNA coding for amino acids 182–188 of human c-myb.

14. The oligonucleotide of claim 13, having a sequence selected from the group consisting of:

```
5'-TGT AGA ATT CCA GTG GTT CTT-3'     [SEQ ID NO:8],
5'-GT AGA ATT CCA GTG GTT CTT-3'      [SEQ ID NO:9],
5'-T AGA ATT CCA GTG GTT CTT-3'       [SEQ ID NO:10],
5'-AGA ATT CCA GTG GTT CTT-3'         [SEQ ID NO:11],
5'-GA ATT CCA GTG GTT CTT-3'          [SEQ ID NO:12],
5'-A ATT CCA GTG GTT CTT-3'           [SEQ ID NO:13],
5'-ATT CCA GTG GTT CTT-3'             [SEQ ID NO:14],
5'-TGT AGA ATT CCA GTG GTT CT-3'      [SEQ ID NO:15],
5'-TGT AGA ATT CCA GTG GTT C-3'       [SEQ ID NO:16],
5'-TGT AGA ATT CCA GTG GTT-3'         [SEQ ID NO:17],
5'-TGT AGA ATT CCA GTG GT-3'          [SEQ ID NO:18],
5'-TGT AGA ATT CCA GTG G-3'           [SEQ ID NO:19],
```
and
```
5'-TGT AGA ATT CCA GTG-3'             [SEQ ID NO:20].
```

15. A method for identifying patients with central nervous system cancer characterized by overexpression of c-myb, comprising:

exposing brain cancer cells obtained from the patient to one or more antisense oligonucleotide complementary to c-myb; and correlating inhibition of growth in said exposed brain cancer cells with overexpression of c-myb.

16. The method of claim 15, wherein inhibition of growth is measured by thymidine incorporation into growing cells.

17. A method according to claim 16, wherein said antisense oligonucleotide is complementary to the nucleic acid sequence encoding amino acids 182 to 188.

\* \* \* \* \*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GTGCCGGGGT CTTCGGGC                                                    18

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TGCCGGGGTC TTCGGGC                                                     17

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCCGGGGTCT TCGGGC                                                      16

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCGGGGTCTT CGGGC                                                       15

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTGCCGGGGT CTTCGGG                                                     17

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTGCCGGGGT CTTCGG                                                      16

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GTGCCGGGGT CTTCG                                                     15
```

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
TGTAGAATTC CAGTGGTTCT T                                              21
```

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GTAGAATTCC AGTGGTTCTT                                                20
```

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
TAGAATTCCA GTGGTTCTT                                                 19
```

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
AGAATTCCAG TGGTTCTT                                                  18
```

(2) INFORMATION FOR SEQ ID NO:12:

(i) SEQUENCE CHARACTERISTICS:
        (A) LENGTH: 17 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:12:

GAATTCCAGT GGTTCTT                                                      17

(2) INFORMATION FOR SEQ ID NO:13:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AATTCCAGTG GTTCTT                                                       16

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

ATTCCAGTGG TTCTT                                                        15

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TGTAGAATTC CAGTGGTTCT                                                   20

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TGTAGAATTC CAGTGGTTC                                                    19

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:17:

TGTAGAATTC CAGTGGTT    18

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TGTAGAATTC CAGTGGT    17

(2) INFORMATION FOR SEQ ID NO:19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TGTAGAATTC CAGTGG    16

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TGTAGAATTC CAGTG    15